United States Patent
Dallerup Rasmussen et al.

(10) Patent No.: US 11,889,813 B2
(45) Date of Patent: Feb. 6, 2024

(54) CASSETTE FOR BIOMARKER ANALYSIS OF A MILK SAMPLE

(71) Applicant: DELAVAL HOLDING AB, Tumba (SE)

(72) Inventors: Claus Dallerup Rasmussen, Tumba (SE); Thomas Nikolai Carlsen, Tumba (SE)

(73) Assignee: DeLaval Holding AB, Tumba (SE)

( * ) Notice: Subject to any disclaimer, the term of this patent is extended or adjusted under 35 U.S.C. 154(b) by 355 days.

(21) Appl. No.: 16/769,131

(22) PCT Filed: Dec. 18, 2018

(86) PCT No.: PCT/SE2018/051335
§ 371 (c)(1),
(2) Date: Jun. 2, 2020

(87) PCT Pub. No.: WO2019/132760
PCT Pub. Date: Jul. 4, 2019

(65) Prior Publication Data
US 2020/0337262 A1    Oct. 29, 2020

(30) Foreign Application Priority Data
Dec. 28, 2017 (SE) .................. 1751660-0

(51) Int. Cl.
*G01N 33/04* (2006.01)
*A01J 5/013* (2006.01)
(Continued)

(52) U.S. Cl.
CPC ............ *A01J 5/0131* (2013.01); *A01J 5/045* (2013.01); *G01N 33/04* (2013.01);
(Continued)

(58) Field of Classification Search
CPC ..... A01J 5/0131; G01N 33/04; G01N 35/021; G01N 2035/00019
See application file for complete search history.

(56) References Cited

U.S. PATENT DOCUMENTS

| 3,604,790 A * | 9/1971 | Land .................. G03B 17/265 352/29 |
| 9,052,293 B2 * | 6/2015 | Miltner ................ A61B 5/1455 |

(Continued)

FOREIGN PATENT DOCUMENTS

| WO | 2004/034063 A2 | 4/2004 |
| WO | 2017/144913 A1 | 8/2017 |

OTHER PUBLICATIONS

International Search Report and Written Opinion, dated Apr. 24, 2019, from corresponding PCT application No. PCT/SE2018/051335.

(Continued)

*Primary Examiner* — Rebecca C Bryant
(74) *Attorney, Agent, or Firm* — NIXON & VANDERHYE

(57) ABSTRACT

A cassette (130) configured to enable measurement of at least one biomarker value of a milk sample of an animal (100). The cassette (130) includes a tape distributing spool (131); a tape (170) with a plurality of dry sticks (180a, 180b, 180c), configured to indicate the biomarker value of the milk sample, and a top film (310) arranged to protect the dry sticks (180a, 180b, 180c) while rolled up on the tape distributing spool (131); a tape collecting spool (132), configured to collect used dry sticks (180a, 180b, 180c); and a top film reel (330), arranged to peel off and collect the top film (310) of the tape (170).

14 Claims, 7 Drawing Sheets

(51) Int. Cl.
*A01J 5/04* (2006.01)
*G01N 35/00* (2006.01)
*G01N 35/02* (2006.01)

(52) U.S. Cl.
CPC ..... *G01N 35/00009* (2013.01); *G01N 35/021* (2013.01); *G01N 2035/00019* (2013.01)

(56) References Cited

U.S. PATENT DOCUMENTS

| | | | |
|---|---|---|---|
| 9,234,883 B2* | 1/2016 | Zahn | G01N 33/49 |
| 2002/0124803 A1 | 9/2002 | Chen et al. | |
| 2003/0211619 A1 | 11/2003 | Olson et al. | |
| 2004/0049123 A1* | 3/2004 | Kuo | A61B 10/0012 |
| | | | 600/551 |
| 2005/0214881 A1* | 9/2005 | Azarnia | G01N 35/00009 |
| | | | 435/7.92 |
| 2006/0260939 A1* | 11/2006 | Anderson | G01N 33/04 |
| | | | 204/403.01 |
| 2007/0217950 A1* | 9/2007 | Kramer | A61B 5/14532 |
| | | | 422/66 |
| 2010/0239137 A1* | 9/2010 | Pugia | G01N 21/274 |
| | | | 382/128 |
| 2011/0178433 A1 | 7/2011 | Mondro et al. | |
| 2013/0108524 A1 | 5/2013 | Porsch et al. | |
| 2014/0135606 A1 | 5/2014 | Yasui | |
| 2015/0065390 A1* | 3/2015 | Bratkovski | G01N 35/00009 |
| | | | 436/172 |
| 2019/0082659 A1 | 3/2019 | Mottram | |
| 2020/0337262 A1* | 10/2020 | Dallerup Rasmussen | G01N 33/04 |

OTHER PUBLICATIONS

SE Search Report, dated Aug. 3, 2018, from corresponding SE application No. 1751660-0.

* cited by examiner

CASSETTE FOR BIOMARKER ANALYSIS OF A MILK SAMPLE

TECHNICAL FIELD

This document discloses a cassette. More particularly, a cassette is described, for enabling measurement of at least one biomarker value of a milk sample of an animal.

BACKGROUND

On an animal farm, it is important to keep the animals healthy in order to enhance milk/meat production. For example, it is important to inseminate animals at an optimal moment in order to successfully fertilise the cow. In case the animal is not successfully inseminated, milk production is affected.

Several biomarker measurements may be made on the animal, such as e.g. measuring levels of progesterone, LDH (Lactate Dehydrogenase), BHB (Beta-Hydroxybutyrat) and urea. Thereby important information concerning e.g. heat detection and/or pregnancy of the individual animal may be made (based on measured progesterone level), as well as mastitis (based on LDH) and ketosis (based on BHB). Also, the energy balance may be estimated (based on urea).

Thereby, a farmer/operator provided with important information concerning each individual animal. However, to perform and analyse biomarker measurements of all individual animals at a farm, e.g. by applying milk samples on prepared dry sticks, and analyse these samples are time consuming for the farmer. It also put high demands on administrative skills on the farmer to distinguish biomarker measurements from different animals; as well as high demands on cleanliness for not allowing a biomarker measurement of a first animal to be contaminated by biological matters of another animal.

It would for these reasons be advantageous for the farmer, if the taking of biomarker measurements on milk samples of different animals could be automated, and thereby minimising or at least reducing the manual work effort of the farmer.

It would be desired to find a way to assist the farmer in analysing his/her animals and enhance production at the farm, relieving him/her from the tedious work of handling a plurality of individual dry sticks which are prepared for detecting biomarker measurements.

SUMMARY

It is therefore an object of this invention to solve at least some of the above problems and facilitate for an operator to measure a biomarker value of a milk sample of an animal.

According to a first aspect of the invention, this objective is achieved by a cassette. The cassette is configured to enable measurement of at least one biomarker value of a milk sample of an animal. The cassette comprises a tape distributing spool. Further, the cassette comprises a tape comprising a plurality of dry sticks, configured to indicate the biomarker value of the milk sample, and a top film arranged to protect the dry sticks while rolled up on the tape distributing spool. Furthermore, the cassette also comprises a tape collecting spool, configured to collect used dry sticks. In addition, the cassette comprises a top film reel, arranged to peel off and collect the top film of the tape.

A biomarker, or biological marker, generally refers to a measurable indicator of some biological state or condition of the animal. The biomarker value measurement may be associated with pregnancy/reproduction of the animal.

By keeping the dry sticks on a tape maintained in a cassette, the unused dry sticks are protected from affection of humidity, moisture in the air, and various impurities that may appear in an agricultural environment. The operator is provided with a convenient solution for automatically making biomarker value measurements with a minimum of required user effort, enabling biomarker value measurements also on a farm having a shortage of operators, and without requiring any particular involvement or skill of the operator.

In a first possible implementation of the cassette according to the first aspect, the cassette may comprise a capstan reel comprising teeth, for engaging with advancement apertures on the tape. Further, the cassette may comprise a rear part and a frontal part. The rear part of the cassette may comprise an aperture, configured to receive a liquid evacuator. Also, the rear part of the cassette may comprise a rear tape distributing spool holding member, arranged to hold the tape distributing spool. Also, the rear part of the cassette may comprise a rear tape collecting holding member, arranged to hold the tape collecting spool. Furthermore, the rear part of the cassette may comprise a rear capstan reel holding member, arranged to hold the capstan reel. The rear part of the cassette may in addition also comprise a rear top film reel holding member, arranged to hold the top film reel. The frontal part of the cassette may comprise a frontal tape distributing spool holding member, arranged to hold the tape distributing spool. Further, the frontal part of the cassette may comprise a frontal tape collecting holding member, arranged to hold the tape collecting spool. In addition, the frontal part of the cassette may comprise a frontal capstan reel holding member, arranged to hold the capstan reel. Also, the frontal part of the cassette may in addition comprise a frontal top film reel holding member, arranged to hold the top film reel.

Thanks to the aperture configured to receive a liquid evacuator at the rear part of the cassette, superfluous liquid, e.g. from rinsing of the needle applying the milk samples, between milk samples from different animals, could be collected and conveyed out of the cassette. Thereby, the risk of carrying over from a milk sample of a first animal, to a milk sample of a second animal is reduced.

In a second possible implementation of the cassette according to the first aspect, or according to the first possible implementation thereof, the cassette also comprises a top lid. The top lid of the cassette may comprise an opening, configured to enable a needle of a dosing module to be inserted for applying the milk sample of the animal to one of the dry sticks, to which the top film has been peeled off.

In a third possible implementation of the cassette according to the first aspect, or according to any previously disclosed possible implementation thereof, the lop lid of the cassette may comprise a pressure exertion member. The pressure exertion member may be arranged to act on the tape to keep it at a predetermined distance from the top lid.

By applying the pressure exertion member, it is asserted that the tape with the dry sticks is at the same distance from both the camera and the needle at the moment of application of the milk sample, leading to that the image captured by the camera is focused and could be correctly analysed. Further, by asserting that the advancement apertures of the tape are kept in place at the teeth on the capstan reel, the feeding of the tape could be made in a smooth and predictable manner.

In a fourth possible implementation of the cassette according to the first aspect, or according to any previously disclosed possible implementation thereof, the top lid may be arranged to act on the tape to keep the advancement apertures on the tape in place at the teeth on the capstan reel.

In a fifth possible implementation of the cassette according to the first aspect, or according to any previously disclosed possible implementation thereof, the cassette may comprise at least one driving belt, arranged to convey driving motion from the capstan reel, to at least one of the spools.

Thereby, a reliable, yet easily mounted solution is provided, ensuring a stable feeding of the tape.

In a sixth possible implementation of the cassette according to the fifth possible implementation of the first aspect, the driving belt may be arranged to convey driving motion from the capstan reel to the tape collecting spool.

In a seventh possible implementation of the cassette according to the first aspect, or according to any previously disclosed possible implementation thereof, the rear part of the cassette may comprise at least one ventilation aperture.

Thanks to the ventilation aperture, the temperature around the dry sticks in the cassette may be kept at the temperature between 10-25 degrees, leading to more reliable results of the biometric measurements. Also, any undesired moisture within the cassette may be evacuated from the cassette by evaporation.

In an eighth possible implementation of the cassette according to the first aspect, or according to any previously disclosed possible implementation thereof, the cassette may be configured to be detachably inserted in a service module, associated with a milking equipment.

By allowing the cassette to be detachably inserted into the service module, it becomes possible to in a convenient manner exchange the cassette, also for the unexperienced operator.

In a ninth possible implementation of the cassette according to the first aspect, or according to any previously disclosed possible implementation thereof, the cassette may comprise a tape supporting member, arranged to guide the tape in a trajectory between the tape distributing spool, and the capstan reel.

Thanks to the tape supporting member, the tape is maintained at the same distance from both the camera and the needle at the moment of application of the milk sample, independently of how much tape that has been distributed from the tape distributing spool. Thereby, the image captured by the camera is focused and could be correctly analysed.

In a tenth possible implementation of the cassette according to the first aspect, or according to any previously disclosed possible implementation thereof, the tape collecting spool of the cassette may comprise guiding edges, arranged to fixate the tape on the tape collecting spool during collection of the tape.

Thereby, any entanglement of the tape during collection of the tape with the used dry sticks is avoided, leading to a dependable and operationally more reliable cassette.

In an eleventh possible implementation of the cassette according to the first aspect, or according to any previously disclosed possible implementation thereof, the rear part, the frontal part, and/or the top lid of the cassette may be made of plastic.

Plastic material of the cassette involves several advantages such as ease to form, low price, and low weight while still protecting the tape and the dry sticks from mechanical damage and humidity.

Further, the plastic could easily be given different colours for different types of biomarker dry sticks; e.g. blue for progesterone measuring dry sticks, red for LDH measuring dry sticks, etc. The risk that the operator enters an incorrect cassette (comprising non-intended biomarker dry sticks) is thereby minimised.

In a twelfth possible implementation of the cassette according to the first aspect, or according to any previously disclosed possible implementation thereof, the cassette may be disposable.

Thanks to the described aspects, biomarker values of milk samples of animals on the farm may be measured in an automatised manner, requiring a minimum of efforts of an operator.

Other advantages and additional novel features will become apparent from the subsequent detailed description.

FIGURES

Embodiments of the invention will now be described in further detail with reference to the accompanying figures, in which.

DETAILED DESCRIPTION

Embodiments of the invention described herein are defined as a cassette, which may be put into practice in the embodiments described below. These embodiments may, however, be exemplified and realised in many different forms and are not to be limited to the examples set forth herein; rather, these illustrative examples of embodiments are provided so that this disclosure will be thorough and complete.

Still other objects and features may become apparent from the following detailed description, considered in conjunction with the accompanying drawings. It is to be understood, however, that the drawings are designed solely for purposes of illustration and not as a definition of the limits of the herein disclosed embodiments, for which reference is to be made to the appended claims. Further, the drawings are not necessarily drawn to scale and, unless otherwise indicated, they are merely intended to conceptually illustrate the structures and procedures described herein.

Figure 1:
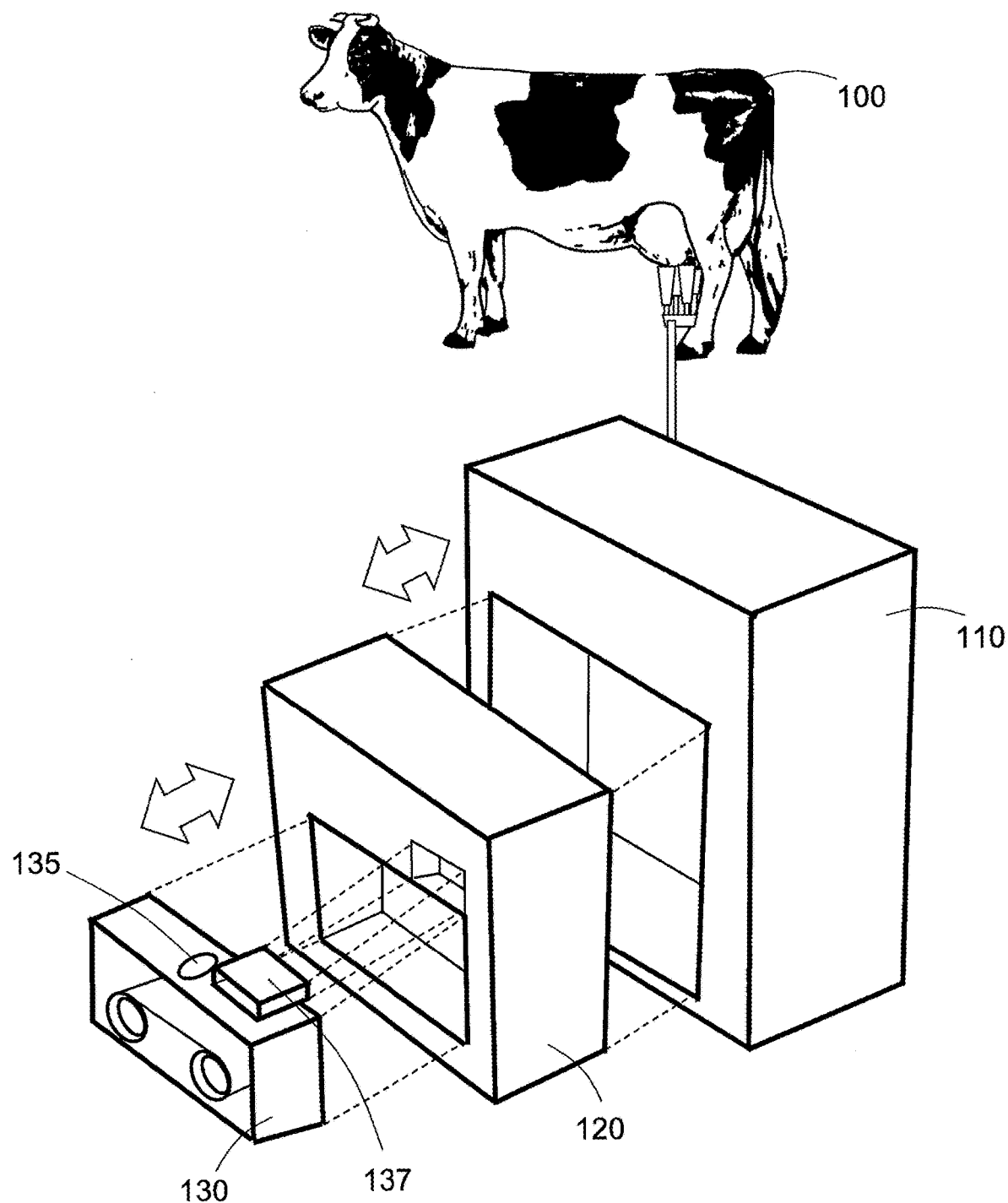
FIG. 1 illustrates an example of an arrangement for measuring a biomarker value of a milk sample of an animal.

FIG. 1 illustrates a scenario with an animal 100 which may be comprised in a herd of dairy animals at a dairy farm.

"Animal" may be any arbitrary type of domesticated female milk producing and/or meat producing mammal such as cow, goat, sheep, horse, camel, dromedary, primate, dairy buffalo, donkey, reindeer, yak, etc.

Milk of the animal 100 may be extracted by a milking equipment such as e.g. a milking robot or other milking arrangement, and provided to a service module 120.

The service module 120 may be releasably inserted into the milking equipment in some embodiments. Thus, there may be an interface between the milking equipment and the service module 120 for providing milk and possibly electricity via the milking equipment to the service module 120.

The service module 120 comprises various electronics and equipment such as a camera, one or several pumps, a tube element for attachment to the interface to the milking equipment, motors, a communication unit etc.

A cassette 130 may be detachably inserted into the service module 120. The cassette 130 comprises a tape with dry sticks, configured to indicate a biomarker value of a milk sample of the animal 100. The cassette 130 may in some embodiments be configured to be detachably inserted in the service module 120 and held in place by a fastening means such as a snap lock, a magnet, a screw, etc., and a door of the service module 120 may be closed for enclosing the cassette 130 within the service module 120, thereby further fixating the cassette 130 in the position.

Thereby, a milk sample of the animal 100 may be extracted from the animal 100 by the milking equipment and provided via the service module 120 to one of the dry sticks on the tape of the cassette 130. The dry sticks may react on presence and/or amount of one or several biomarkers, e.g. by changing colours, or intensity of a colour. The camera in the service module 120 may capture an image through an opening 135 in the cassette 130. The captured image of the dry stick may then be analysed by a control unit, and based on the intensity of the colour, presence and/or quantity of the biomarker in the milk sample may be estimated.

The measured biomarker may be e.g. progesterone, glycoprotein, oestrogen and/or Gonadatropin-Releasing Hormones, or any other similar biomarker associated with reproduction of the animal 100, in different embodiments.

Progesterone is a hormone that regulates several physiological functions of the animal 100. Progesterone may prepare the uterus for pregnancy, maintain the pregnancy if fertilisation occurs, and inhibit the animal 100 from showing signs of standing oestrus and ovulating when pregnant. Progesterone levels, for example, may rise at the beginning of the pregnancy, and be kept at a high level throughout the pregnancy of the animal 100. Progesterone levels in milk samples may be used to monitor pregnancy, oestrous cycles (heat detection) and/or postpartum ovarian activity. For these reasons, progesterone levels of animals 100 at the farm is interesting for the operator to detect and keep track of.

However, the measured biomarker may in some embodiments comprise LDH (Lactate Dehydrogenase), BHB (Beta-HydroxyButyrat), urea, and/or somatic cell count; or other biomarker related to status of the animal 100. In some embodiments, a plurality of the above enumerated biomarkers may be measured. Alternatively, in some embodiment, the operator may subscribe to a cassette 130 comprising a certain dry stick on the tape configured to measure a biomarker, or a set of biomarkers, as selected by the farmer; and/or different cassettes 130 comprising dry sticks on the tape configured to measure different biomarkers, or sets of biomarkers, during different periods of time of the year.

In some embodiments, a dosing module 137 may also be detachably inserted into the service module 120. The dosing module 137 may comprise for example a needle, and/or one or several pumps. A diluent container with diluent may be external to the dosing module 137.

Figure 2A:
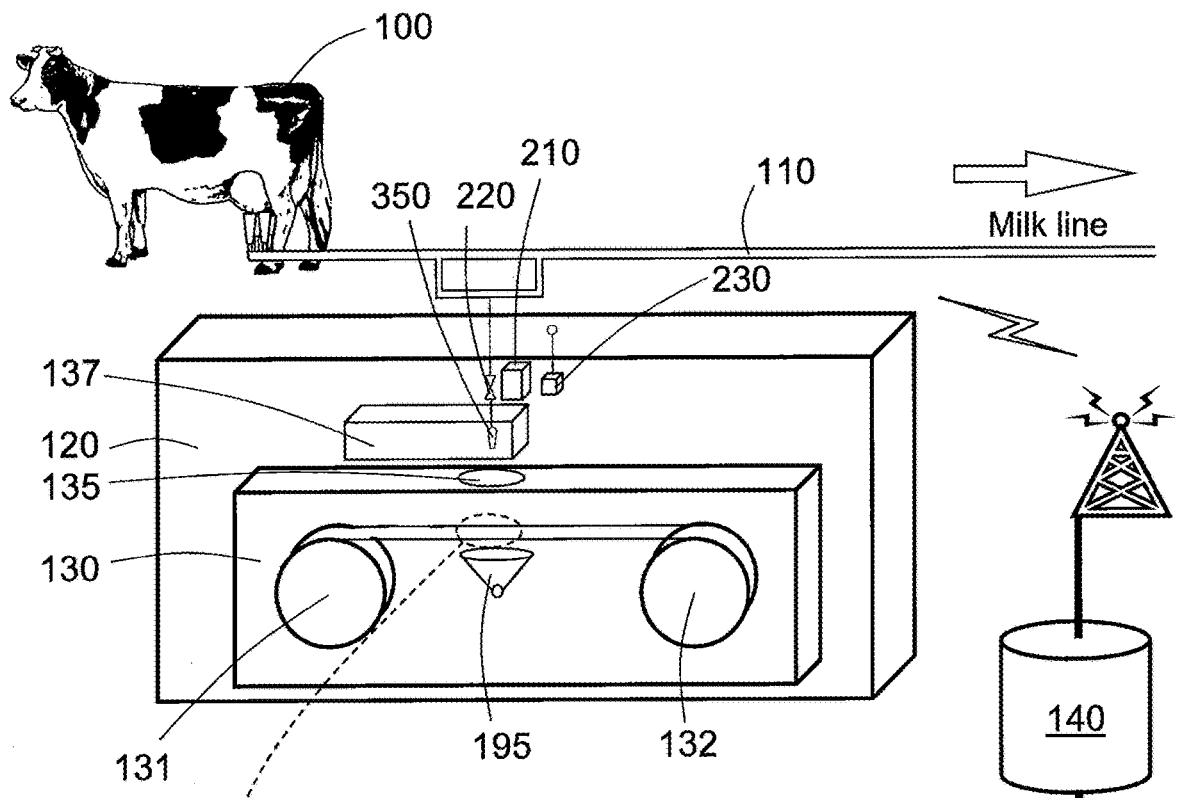
FIG. 2A illustrates a cassette inserted into a service module, according to an embodiment.

FIG. 1 and FIG. 2A depict general overviews of the environment in which the tape according to the provided solution is intended to operate, without going too much into details, in order for the reader to get a rough overview. Sublime examples of details of the involved entities, in particular the cassette 130 and the tape, and how they interact with each other may be fully enjoyed in FIG. 2B, FIGS. 3A-3B, FIG. 4, and FIGS. 5A-5B.

FIG. 2A illustrates a scenario illustrating a service module 120, a cassette 130, and a dosing module 137, according to an embodiment. The service module 120 comprises electronics and equipment such as e.g. a camera 210, a tube element 220 for attachment to the milking equipment, a motor, a communication unit 230, etc., to be used for determining a biometric value of a milk sample received from an animal 100. In some embodiments, the dosing module 137 may comprise one or several pumps configured to act on the tube element 220 for advancing the milk sample through the tube element 220.

In the illustrated embodiment, the dosing module 137 may comprise a needle 350 for applying the milk sample to a dry stick 180a, 180b, 180c on a tape 170 in the cassette 130 through an opening 135 in the cassette 130. The camera 210 may then align the needle 350 with the dry stick 180a, 180b, 180c on the tape 170 of the cassette 130.

The camera 210 of the service module 120 may capture an image of the dry sticks 180a, 180b, 180c of the carrier tape 170 through the opening 135, and based on these images, a cassette external motor may adjust the tape 170 for positioning a new dry sticks 180a, 180b, 180c, on which a new test is to be made, in relation to the needle 350.

The communication unit 230 may communicate via a wired or wireless communication interface, with a control unit 150, a database 140, and/or an output unit 160.

Such wireless communication interface may comprise, or at least be inspired by wireless communication technology such as 3GPP LTE, Bluetooth (BT) to name but a few possible examples of wireless communications in some embodiments.

The camera 210 of the service module 120 is configured to inspect one dry stick 180a, 180b, 180c on the tape 170 of the cassette 130, through the opening 135 of the cassette 130. The camera 210 may also assist in alignment of the needle 350 and the position of the dry stick 180a, 180b, 180c on the tape 170, by adjusting the tape 170.

Further, the service module 120 also comprises a tube element 220 configured to receive the milk sample of the animal 100 via a milking equipment and provide the milk sample to a needle 350, i.e. the needle 350 comprised in the dosing module 137.

The dosing module 137 may in addition comprise at least one pump in some embodiments, configured to act on the tube element 220 for providing the milk sample to the needle 350. The pump may thus act on the tube element 220 to get the milk sample to propagate through the tube element 220, to reach the needle 350; or the mixing chamber 355 of the needle 350. The mixing chamber 355 may alternatively be external to the needle 350.

The dosing module 137 may also comprise a liquid evacuator or drainage 195, which may collect liquid that has been output by the needle 350. The liquid, when comprising merely milk, may be returned back to the milk line in some embodiments. In other embodiments, when the milk has been mixed with diluent, the liquid may be conveyed away from the cassette 130 in order not to soak or contaminate other, unused, dry sticks 180a, 180b, 180c of the tape 170 on the cassette 130.

The control unit 150 is configured to determine a biomarker value of the milk sample of the animal 100, based on an analysis of the image, captured by the camera 210. The control unit 150 may be comprised in the service module 120 in some embodiments; or be external to the service module 120.

The database 140 may store measured biometric values of the animal 100, associated with an identity reference of the animal 100 and/or a time stamp of the measurement. Other measurements and/or data related to the animal 100 may also be stored in the database 140, such as milk yield, e.g. measured by the milk flow meter, activity, breed, parity, rumination, lactation, resting, feed intake, energy balance, Days In Milk, milk production, age and possibly other similar animal status related parameters.

The output unit 160 may be e.g. a cellular mobile telephone, a stationary or portable computing device, a computer tablet, a display, a pair of intelligent glasses, a smart contact lens, an augmented reality device, a smart watch or similar device having a user interface and wireless communication ability.

Via the output unit 160, an operator may take part of the result of the biomarker measurement of the milk sample. The operator is thereby able to analyse the status of the animal 100, such as e.g. if the animal 100 is in heat, in case progesterone is measured.

When a deviation, exceeding a first threshold limit, is detected between the outcomes of the biomarker measurement and the corresponding reference value, an alert may be outputted to the operator. The alert may comprise e.g. visual information, an audio message, a tactile signal or a combination thereof, encouraging the operator to further investigate the reasons for the detected deviation in result. In case a plurality of people is working with the herd, a broadcast may be made to the plurality of operators and their respective associated output units 160, in some embodiments.

Figure 2B:
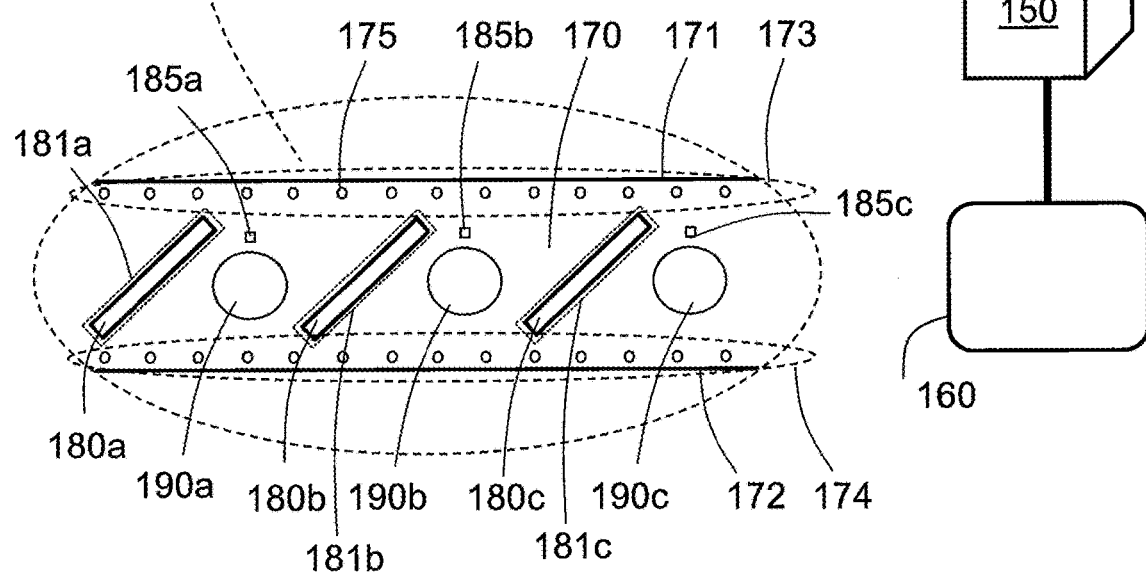
FIG. 2B illustrates a section of a tape comprising dry sticks, according to an embodiment.

FIG. 2B illustrates a tape 170 according to an embodiment. The cassette 130, which may be releasably inserted into the service module 120, comprises the tape 170, which in turn comprises a plurality of dry sticks 180a, 180b, 180c.

The dry sticks 180a, 180b, 180c may be arranged with an inclination a in relation to an axis 197, orthogonal to a longitudinal axis 196 of the tape 170. The inclination a may for example be 15 degrees or there about, or e.g. 10-30 degrees in some embodiments.

An opening 190a, 190b, 190c, may be arranged between at least some of the dry sticks 180a, 180b, 180c, on the tape 170, or on a bottom film of the tape 170, i.e. between the welded seams 181a, 181b, 181c of at least some of the dry sticks 180a, 180b, 180c on the bottom film. The opening 190a, 190b, 190c is configured to convey liquid away from the dry sticks 180a, 180b, 180c during cleaning, or before applying the milk sample to the dry stick 180a, 180b, 180c.

Milk of a first animal 100 may contaminate a milk sample of another, subsequently tested animal. To avoid contamination, or carry over, the tubings and the needle 350 may be flushed with milk of the animal to be tested before the milk sample is applied to the dry stick 180a, 180b, 180c. For avoiding that the flushed milk of the animal to be tested soaks and/or contaminate other unused dry sticks 180a, 180b, 180c, the flushing may be made through the opening 190a, 190b, 190c of the tape 170, e.g. by lowering the needle 350 through the opening 190a, 190b, 190c, and capture the flushed milk with a liquid evacuator 195. The liquid evacuator 195 may then via a tube convey liquid away from the cassette 130.

The tape 170, or the bottom film of the tape 170 may further comprise a reference mark 185a, 185b, 185c, configured to assist a camera 210 in finding the dry stick 180a, 180b, 180c. The reference mark 185a, 185b, 185c may comprise e.g. a hole, a colour mark, a barcode, a simple geometry, or similar.

The reference mark 185a, 185b, 185c may also assist the camera 210 in determining the advancement of the top film reel, to peel off the top film of the dry stick 180a, 180b, 180c, enough to enable application of the milk sample to the dry stick 180a, 180b, 180c, while not peeling off the top film of the next dry stick 180a, 180b, 180c.

Further, the tape 170, or the bottom film of the tape 170 may comprise a first group 173 of advancement apertures 175, arranged at a first edge 171 of the tape 170; and a second group 174 of advancement apertures 175, arranged at a second edge 172 of the tape 170, or the bottom film of the tape 170.

Each dry stick 180a, 180b, 180c may be separately arranged on the tape 170, or the bottom film of the tape 170, by a welded seam 181a, 181b, 181c, and wherein the sealed dry sticks 180a, 180b, 180c are arranged on a distance from each other.

Figure 3A:
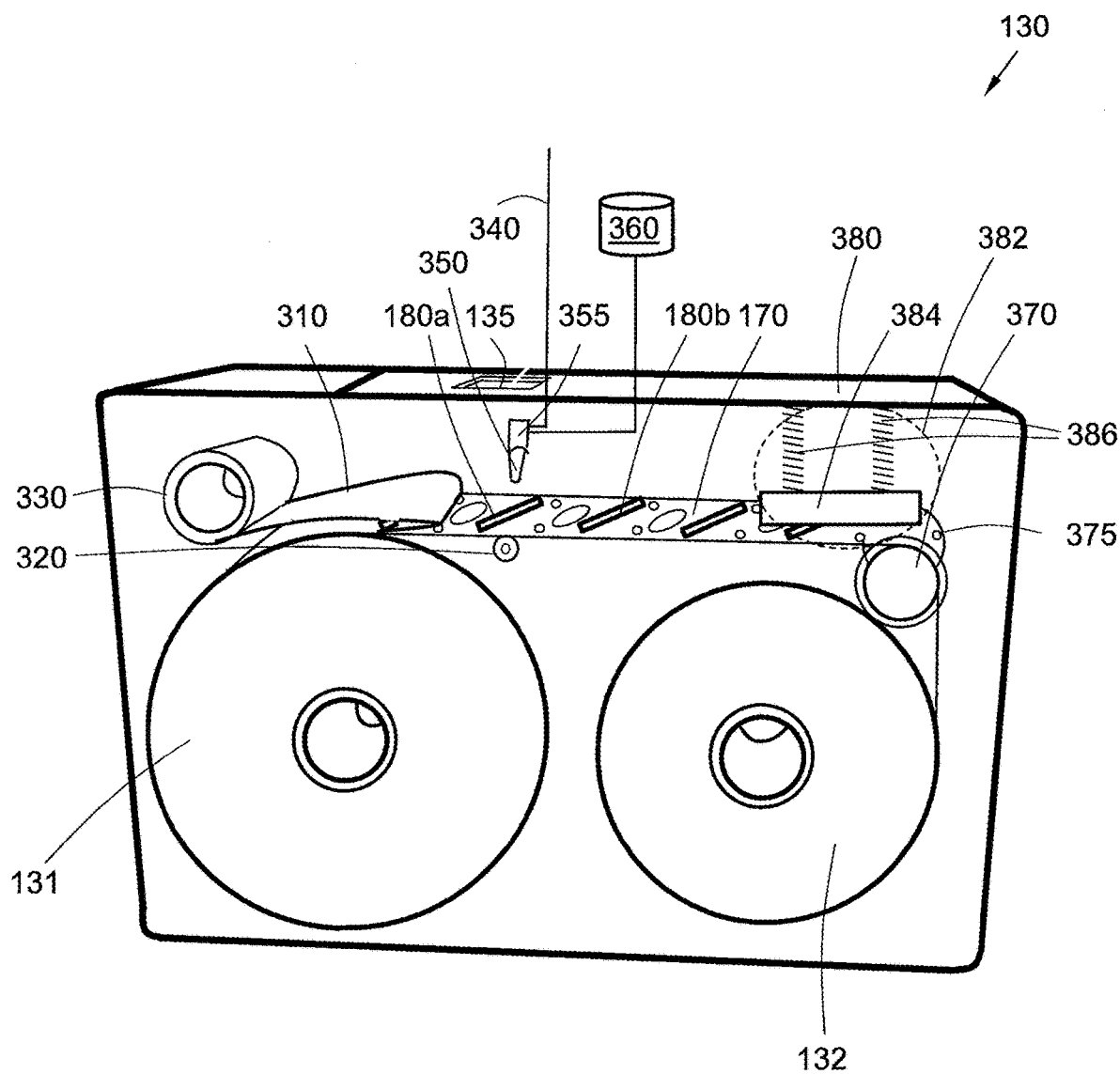
FIG. 3A illustrates a cassette, according to an embodiment.

FIG. 3A illustrates a cassette 130, comprising a tape 170 with dry sticks 180a, 180b, 180c separately, i.e. individually, arranged on the tape 170 at a distance from each other.

In the illustrated embodiment, the tape 170 comprises a bottom film, comprising the dry sticks 180a, 180b, 180c, covered with a top film 310 configured to seal the dry sticks 180a, 180b, 180c on the tape 170.

Also, in the illustrated embodiment, a top film reel 330 is comprised, arranged to peel off and collect the top film 310 of the tape 170. The top film 310 may be peeled off just before the milk sample is to be applied to the peeled off dry stick 180a, 180b, 180c.

Further, the cassette 130 may comprise a capstan reel 370 comprising teeth 375, for engaging with advancement apertures 175 on the tape 170.

The cassette 130 may in addition also comprise a top lid 380, comprising the opening 135, configured to enable the needle 350 of the service module 120 to be inserted for applying the milk sample of the animal 100 to one of the dry sticks 180a, 180b, 180c, to which the top film 310 has been peeled off.

The top lid 380 may comprise at least one pressure exertion member 382, arranged to act on the tape 170 to keep it at a predetermined distance from the top lid 380. Thereby, the camera 210 may be focused on the dry stick 180a, 180b, 180c, as they are constantly situated at the same distance from the camera 210. The pressure exertion member 382 may comprise a spring 386, or a flexible material, and a tape interface unit 384.

Also, the top lid 380 may act on the tape 170 to keep the advancement apertures 175 on the tape 170 in place at the teeth 375 on the capstan reel 370. The form of the top lid 380 may thus have a shape keeping the advancement apertures 175 on the tape 170 in place at the teeth 375 on the capstan reel 370.

Some embodiments of the cassette 130 may comprise a tape supporting member 320, arranged to guide the tape 170 in a trajectory between the tape distributing spool 131, and the capstan reel 370. The tape supporting member 320 may ascertain that the tape 170 is kept at the predetermined distance from the camera 210, thereby enabling the camera 210 to be focused on the dry stick 180a, 180b, 180c.

In some embodiments, the tape 170 may comprise e.g. 300-700 dry sticks 180a, 180b, 180c, or preferably about 400-600 dry sticks 180a, 180b, 180c. Thereby, the tape 170 of the cassette 130 may comprise enough dry sticks 180a, 180b, 180c for testing milk samples of an average automatic milking robot for about a month. The cassette 130 with the tape 170 and the dry sticks 180a, 180b, 180c may then be wasted and exchanged for another one, e.g. through a service subscription. In some embodiments, the cassette 130 may be recycled; i.e. the used cassette 130 may be opened and the used tape 170 may be removed from the used cassette 130. Then, a new, unutilised tape 170 with dry sticks 180a, 180b, 180c may be inserted into the cassette 130, and the cassette 130 may be reassembled.

The dry sticks 180a, 180b, 180c may be designed for one-time usage each. In some embodiments, the dry sticks 180a, 180b, 180c of the tape 170 may be configured to change colour or colour nuance when exposed to the biomarker.

The camera 210 in the service module 120 may capture an image of the dry sticks 180a, 180b, 180c in question, after a predetermined or configurable time period. The colour, or colour intensity of the dry stick 180a, 180b, 180c on the captured image may then be analysed by the control unit 150, where different colour intensities may be associated with a certain biomarker level of the milk sample.

The milk sample may in some embodiments be mixed with a diluent before being applied to the dry sticks 180a, 180b, 180c on the tape 170, e.g. in the mixing chamber 355.

In embodiments, wherein the diluent is kept in a separate container 360 in a separate entity, the operator may change the cassette 130, the dosing module 137, and/or the diluent container 360 at different time intervals. In a non-limiting example, the cassette 130 may be changed once a month while the dosing module 137 comprising the needle 350 may be changed twice a year. In some embodiments, the diluent container 360 may be changed e.g. every second month, every third month, etc. In some embodiments, the operator may refill the diluent, which may reduce overall costs of the operator. Yet an advantage by having multiple replaceable entities such as the cassette 130, the dosing module 137, the diluent container 360, etc., is that in case a fabrication error or a transportation damage occur of a therein comprised entity, such as e.g. the needle 350, only that particular replaceable entity (cassette 130, dosing module 137, diluent container 360, etc.) comprising the defect entity has to be exchanged, which saves resources.

In some embodiments, the dosing module 137 may comprise at least one pump configured to act on the tube element 220 for providing the milk sample to the needle 350; and a second pump configured to provide diluent to a mixing chamber 355.

The ratio of milk and diluent may be adjusted by changing the respective pump speed of one or both liquids, i.e. milk/diluent respectively, in case each liquid is associated with a respective pump.

The needle 350 comprised in the dosing module 137 may comprise the mixing chamber 355 configured to mix obtained diluent with the milk sample before applying the mixed milk sample to the one dry stick 180a, 180b, 180c, in some embodiments. Alternatively, the milk and the diluent may be mixed in a separate mixing chamber 355 in some embodiments.

In some embodiments, the cassette 130 and/or the dosing module 137 may be sealed from the environment and thereby create a climate chamber, wherein a climate environment prevails in the cassette 130/dosing module 137. The cassette 130/dosing module 137 thereby becomes isolated from environmental impact of dust, dirt, liquids, etc., of the farm.

When the tape 170 is moved for placing the dry stick 180a, 180b, 180c to be used in position aligned with the needle 350, the milk/diluent mix may be applied on the dry stick 180a, 180b, 180c.

An advantage of the disclosed solution, by making a division between a service module 120 comprising camera, motor, pumps and other electronics and/or apparatuses; and one or several cassettes or modules 130, 137, 360 comprising disposable material, the solution becomes very easy to use for the operator.

The cassette 130 may comprise dry sticks 180a, 180b, 180c etc., for supporting the farm for a certain predetermined period of time, such as e.g. a month, two months, etc. Before the end of that time period, a supplier may provide a new cassette 130 to the farm, which the operator easy may put into the service module 120, without having to interact with the sensible electronics of the service module 120. The used cassette 130 may then be disposed.

In case a hardware failure or other malfunction occur, the operator may remove the service module 120 from the milking equipment (and also remove the cassette 130 from the service module 120) and provide the service module 120 to a service supplier for reparation/adjustment. During the time period the service module 120 is on repair, the operator may borrow another service module 120 from the service supplier, for example. Thereby, biomarker values of the animals 100 may be determined without interruptions, also when the service module 120 or any part thereof is malfunctioning. Also, as no external technician is required to visit the farm, neither for changing the disposable cassette 130, or the dosing module 137, nor for analysing errors in the service module 120, costs for service and maintenance are minimised or at least reduced.

Figure 3B:
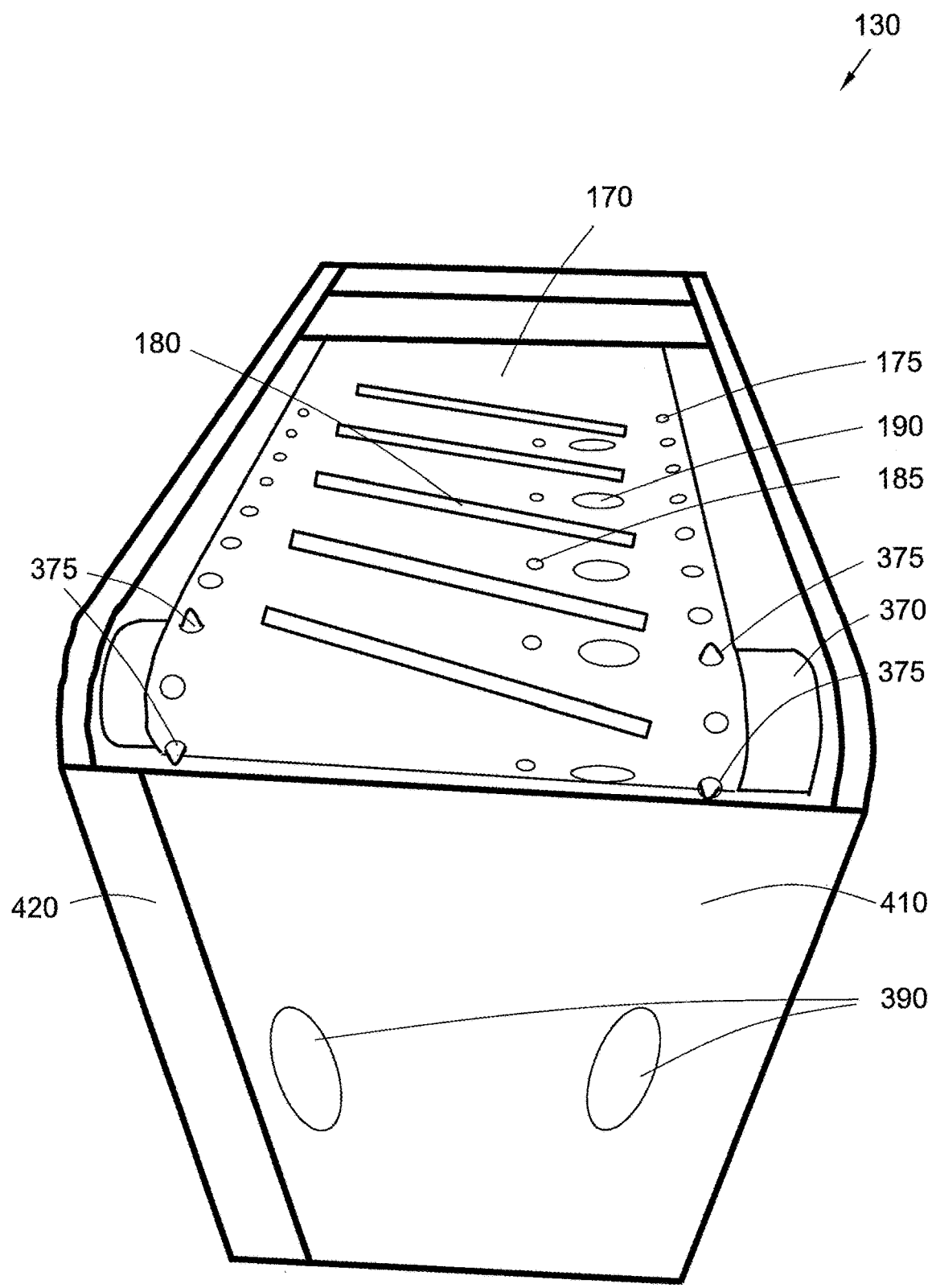
FIG. 3B illustrates a cassette, according to an embodiment.

FIG. 3B illustrates a cassette 130, as regarded from one of the short sides, with the top lid 380 removed. The cassette 130 may be constructed by a rear part 410 and a frontal part 420. The rear part 410, the frontal part 420, and/or the top lid 380 (if any) may be made of plastic, such as a thermoplastic, a thermosetting polymer, etc. Some examples may be e.g. acrylic, acrylonitrile butadiene styrene, polylactide, polybenzimidazole, polycarbonate, polyoxymethylene, polyaryletherketone, polyetherimide, polyethene, polypropylene, polystyrene, polyvinyl chloride, etc. Preferably, the plastic may comprise bioplastic, or green plastic, i.e. comprise a plastic material which is degradable, biodegradable, and/or compostable.

The cassette 130 may comprise a capstan reel 370 configured to move, i.e. forward the tape 170 when the capstan reel 370 is rotated. The capstan reel 370 comprises teeth 375, for engaging with advancement apertures 175 on the tape 170.

The interaction of the teeth 375 of the capstan reel 370, with the advancement apertures 175 on the tape 170 may here be regarded. By rotating the capstan reel 370, the tape 170 is advanced, from the tape distributing spool 131, to the tape collecting spool 132 which is configured to collect used dry sticks 180a, 180b, 180c.

The tape 170 may be arranged on a tape distributing spool 131 and a tape collecting spool 132 of the cassette 130, which spools 131, 132 may be arranged in the cassette 130, and be configured to cooperate with at least one cassette external motor for positional adjustment of the carrier tape 170. The cassette external motor may be comprised in the service module 120 in some embodiments. The cassette external motor may actuate on the capstan reel 370 and/or the top film reel 330. Further, at least one driving belt may be applied on the capstan reel 370 and at least one of the spools 131, 132 for convey driving motion of the cassette external motor, via the capstan reel and the driving belt, to the spools 131, 132. In some embodiments, the driving belt may be arranged to convey driving motion from the capstan reel 370 to the tape collecting spool 132. Thereby, the position of the dry sticks 180a, 180b, 180c on the tape 170 in relation to the opening 135 may be adjusted by advancing the tape 170 via the cassette external motor or motors, by rotating the tape collecting spool 132 of the cassette 130.

In some embodiments, the rear part 410 of the cassette 130 may comprise at least one ventilation aperture 390. Thereby, temperature within the cassette 130 may be kept at the same level between about 10-25 degrees, or approximately the same level as the surrounding environment. In case the environmental temperature is lower than 10 degrees, heated air may be applied and entered into the ventilation apertures 390 for keeping the temperature around the dry sticks 180a, 180b, 180c above 10 degrees. In the opposite case, i.e. the environmental temperature exceeds about 25 degrees, cooled air e.g. from an air conditioner may be applied and entered into the ventilation apertures 390 for keeping the temperature around the dry sticks 180a, 180b, 180c below 25 degrees.

Further, any entered humidity within the cassette 130 may be evaporated through the ventilation aperture 390.

Figure 4:
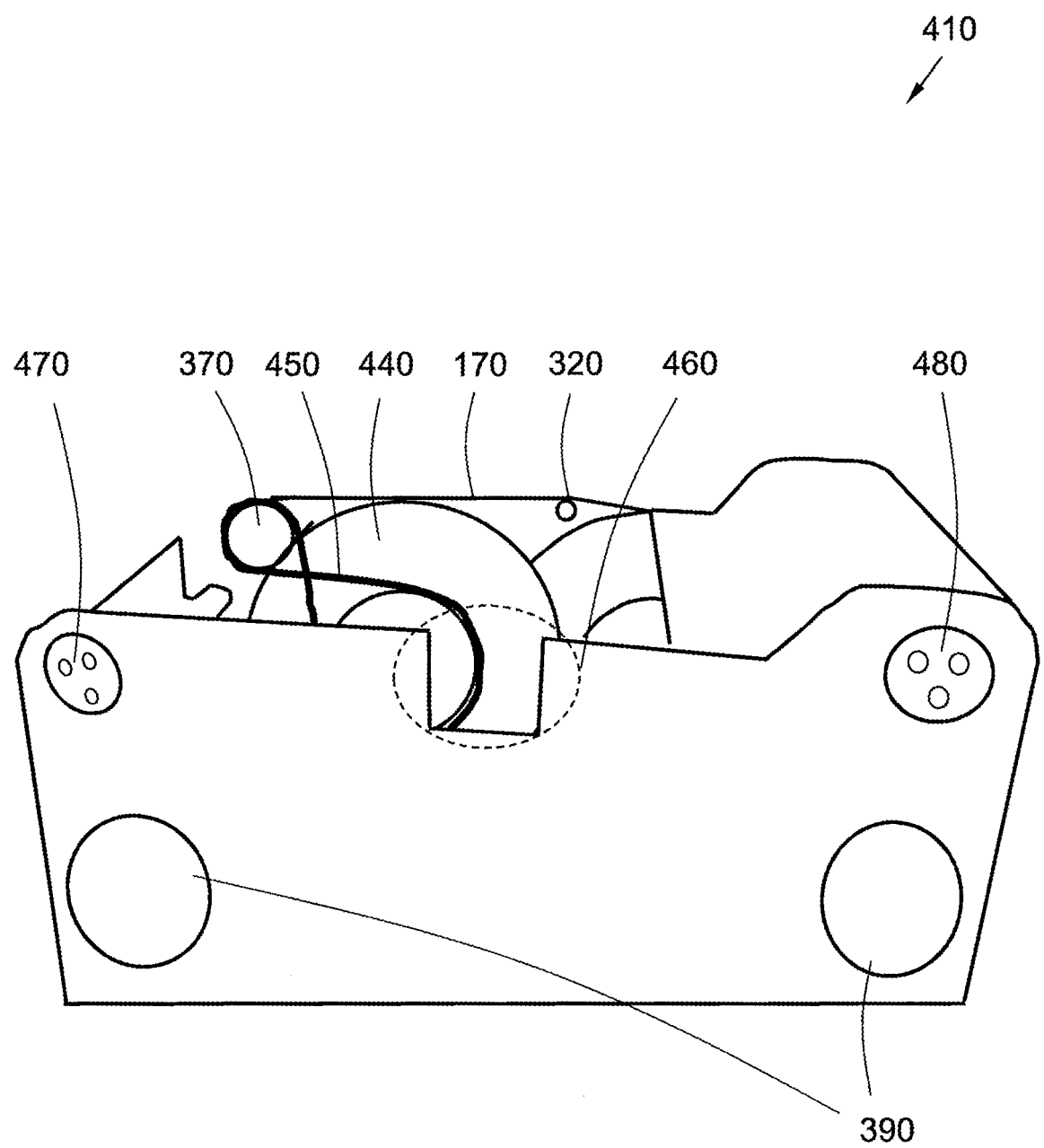
FIG. 4 illustrates a rear part of a cassette, as regarded from the back, according to an embodiment.

FIG. 4 illustrates the rear part 410 of the cassette 130 as regarded from the back side, with the rear lid 380 removed. In the illustrated embodiment, the rear part 410 may comprise at least one ventilation aperture 390 on the rear side of the cassette 170. Thereby, the risk of humidity, dirt, dust, etc., entering the ventilation aperture 390 is eliminated, minimised or at least reduced by having the ventilation on the rear side of the cassette 130.

The capstan reel 370 and the top film reel 330 may be rotated by a respective engine of the service module 120. The rear lateral part 410 also may comprise a first drive axle interface 470, arranged to rotate the capstan reel 370 when the engine of the service module 120 acts on the first drive axle interface 470. In some embodiments, a driving belt 450 may be arranged to convey driving motion from the capstan reel 370, to one of the spools 131, 132. The driving belt 450 may be arranged in order to reverse the rotational direction of the spool 131, 132, in relation to the capstan reel 370. The driving belt 450 may be made of a somewhat flexible material such as rubber, or synthetic polymers e.g. polyurethane. The driving belt 450 may have an approximately circular cross section, or be a flat belt, a V-belt, a polygroove belt, a ribbed belt, etc. In order to turn the rotational direction of the spool 131, 132, the driving belt 450 may be twisted in an 8-shaped loop around the capstan reel 370 and the spool 131, 132.

In some embodiments, the rear lateral part 410 also may comprise a second drive axle interface 480, arranged to rotate the top film reel 330.

The cassette 130 may comprise a tape supporting member 320, arranged to guide the tape 170 in a trajectory between the tape distributing spool 131, and the tape collecting spool 132.

Furthermore, the tape collecting spool 132 of the cassette 130 may comprise guiding edges 440, arranged to laterally fixate the tape 170 on the tape collecting spool 132, as it is rolled up on the tape collecting spool 132.

The rear part 410 of the cassette 130 also may comprise an aperture 460, configured to receive a liquid evacuator 195 of a dosing module 137 or a service module 120, for conveying away liquid from the cassette 130.

Figure 5A:
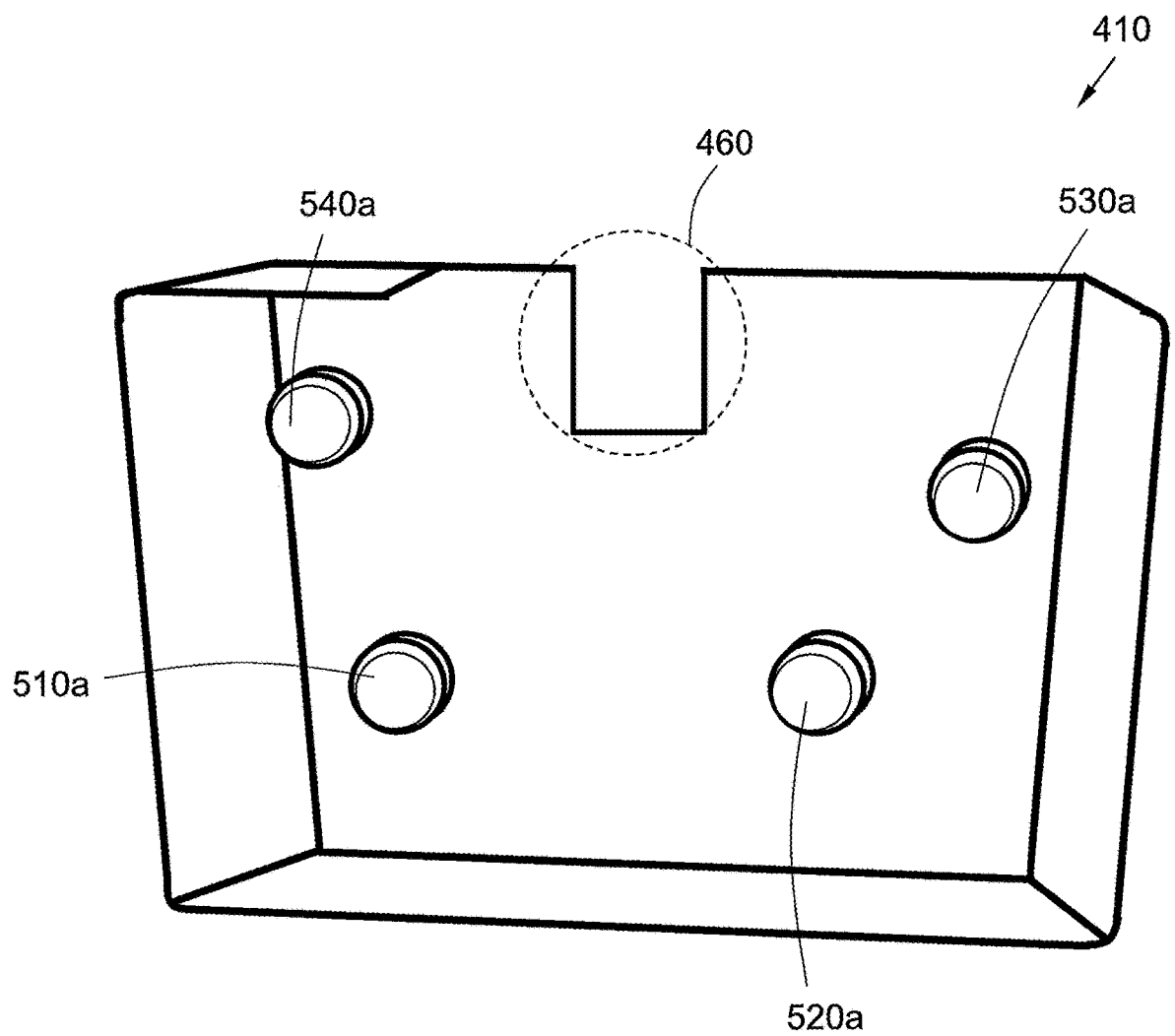
FIG. 5A illustrates a rear part of a cassette, as regarded from the inside, according to an embodiment.

FIG. 5A illustrates the rear part 410 of the cassette 130 as regarded from the interior side; i.e. the opposite side of the rear part 410, as is illustrated in FIG. 4.

The rear part 410 may comprise an aperture 460, configured to receive a liquid evacuator 195. Further, the rear part 410 of the cassette 130 may comprise a rear tape distributing spool holding member 510a, arranged to hold the tape distributing spool 131. Also, the rear part 410 of the cassette 130 may comprise a rear tape collecting holding member 520a, arranged to hold the tape collecting spool 132. The rear part 410 of the cassette 130 may also comprise a rear capstan reel holding member 530a, arranged to hold the capstan reel 370. Furthermore, the rear part 410 of the cassette 130 may comprise a rear top film reel holding member 540a, arranged to hold the top film reel 330.

Figure 5B:
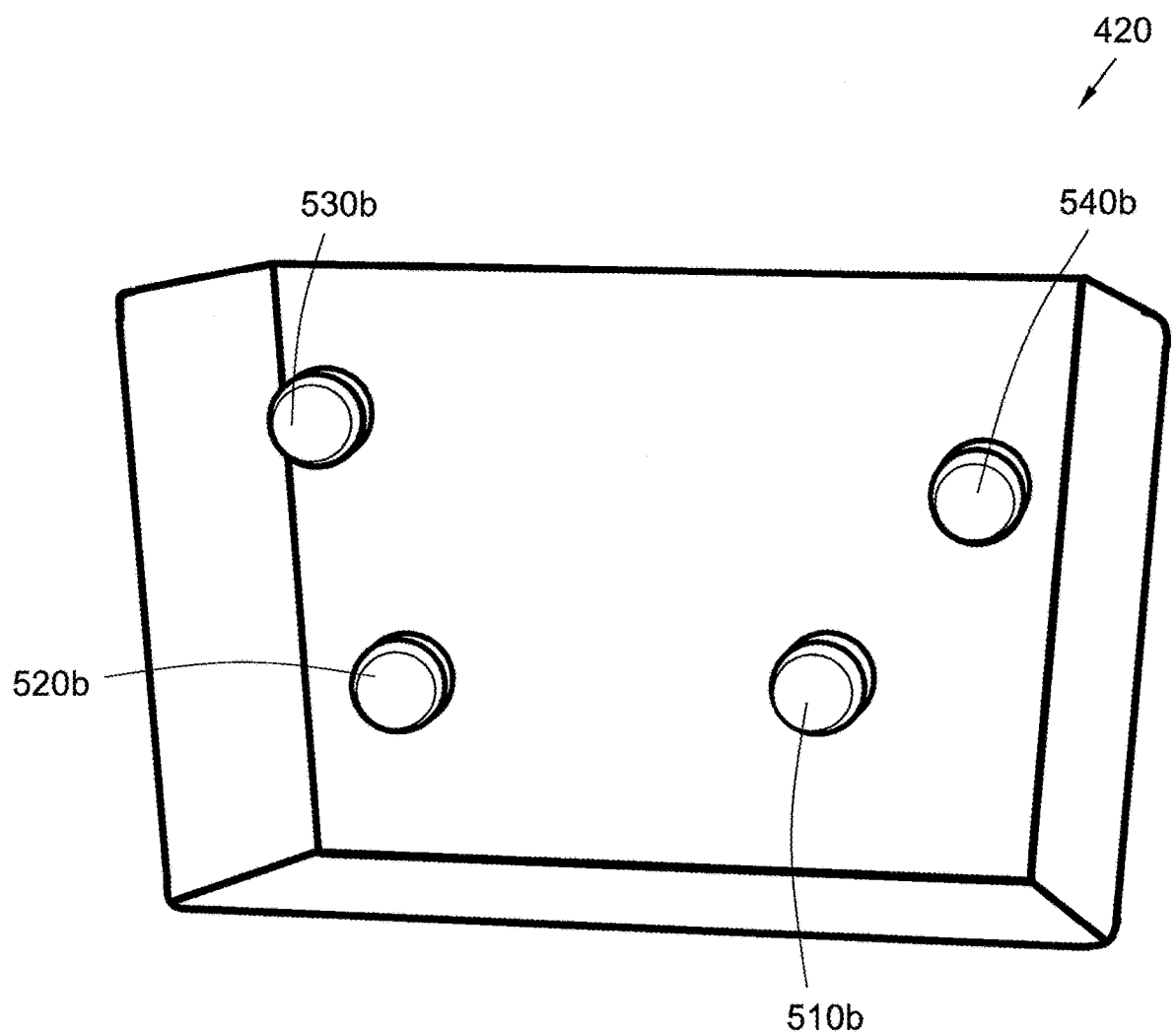
FIG. 5B illustrates a frontal part of a cassette, as regarded from the inside, according to an embodiment.

FIG. 5B illustrates a frontal part 420 of the cassette 130 as regarded from the interior side.

The frontal part 420 of the cassette 130 may comprise a frontal tape distributing spool holding member 510b, arranged to hold the tape distributing spool 131. Further, the frontal part 420 of the cassette 130 may comprise a frontal tape collecting holding member 520b, arranged to hold the tape collecting spool 132. The frontal part 420 of the cassette 130 may also comprise a frontal capstan reel holding member 530b, arranged to hold the capstan reel 370. Furthermore, frontal part 420 of the cassette 130 may also comprise a frontal top film reel holding member 540b, arranged to hold the top film reel 330.

The embodiments, or parts thereof, illustrated in FIG. 1, FIG. 2A, FIG. 2B, FIG. 3A, FIG. 3B, FIG. 4, FIG. 5A, and/or FIG. 5B may with advantage be combined with each other for achieving further benefits.

The terminology used in the description of the embodiments as illustrated in the accompanying drawings is not intended to be limiting of the described cassette 130, tape 170, service module 120, control unit 150, and/or dosing module 137. Various changes, substitutions and/or alterations may be made, without departing from invention embodiments as defined by the appended claims.

As used herein, the term "and/or" comprises any and all combinations of one or more of the associated listed items. The term "or" as used herein, is to be interpreted as a mathematical OR, i.e., as an inclusive disjunction; not as a mathematical exclusive OR (XOR), unless expressly stated otherwise. In addition, the singular forms "a", "an" and "the" are to be interpreted as "at least one", thus also possibly comprising a plurality of entities of the same kind, unless expressly stated otherwise. It will be further understood that the terms "includes", "comprises", "including" and/or "comprising", specifies the presence of stated features, actions, integers, steps, operations, elements, and/or components, but do not preclude the presence or addition of one or more other features, actions, integers, steps, operations, elements, components, and/or groups thereof. A single unit such as e.g. a processor may fulfil the functions of several items recited in the claims. The mere fact that certain measures or features are recited in mutually different dependent claims, illustrated in different figures or discussed in conjunction with different embodiments does not indicate that a combination of these measures or features cannot be used to advantage. A computer program may be stored/distributed on a suitable medium, such as an optical storage medium or a solid-state medium supplied together with or as part of other hardware, but may also be distributed in other forms such as via Internet or other wired or wireless communication system.

The invention claimed is:

1. A cassette (130) configured to enable measurement of at least one biomarker value of a milk sample of milk extracted by a milking equipment (110) from an animal (100), the milking equipment (110) providing extracted milk to a service module (120) having a camera (210);

the cassette (130) being disposable and comprising:
a housing providing the cassette with an interior volume, the housing being insertable into the service module (12),
wherein the housing comprises a top lid (380) having an opening (135), a rear part (410), and a frontal part (420),
the top lid (380) forming a side of the housing extending between the rear part (410) and the frontal part (420),
the rear part (410), the frontal part (420), the top lid (380) each being made of plastic;
wherein, the opening (135) of the housing is a camera alignment opening;
a tape distributing spool (131) located within the housing;
a tape (170) rolled up on the tape distributing spool (131), the tape (170) comprising a plurality of dry sticks (180a, 180b, 180c), configured to indicate the biomarker value of the milk sample, and a top film (310) arranged to protect the dry sticks (180a, 180b, 180c) while rolled up on the tape distributing spool (131), the tape (170) comprising advancement apertures (175) and being advanceable within the housing so that each of the dry sticks (180a, 180b, 180c) are individually aligned with the opening (135) to respectively receive the milk sample when in alignment with the opening (135) onto each of the dry sticks (180a, 180b, 180c) and so that each of the dry sticks (180a, 180b, 180c) are subsequently individually aligned with the opening (135);
a tape collecting spool (132) located within the housing, the tape collecting spool (132) configured to collect the tape (170) with used dry sticks (180a, 180b, 180c);
a top film reel (330) located within the housing, the top film reel arranged to peel off and collect the top film (310) of the tape (170); and
a capstan reel (370) comprising teeth (375), for engaging with the advancement apertures (175) on the tape (170),
wherein the tape (170) extends in a trajectory between the tape distributing spool (131) and the capstan reel (370),
wherein the opening (135) is located above the tape (170) and vertically aligned with one of the dry sticks (180a, 180b, 180c) with the one of the dry sticks (180a, 180b, 180c) being visible through the opening (135),
wherein the tape (170) is located above the tape distributing spool (131) and the tape collecting spool (132) such that the tape (170) is positioned with respect to the opening (135) to i) enable a needle (350) of a dosing module (137) to be inserted through the opening (135) for applying the milk sample of the animal (100) to the one of the dry sticks (180a, 180b, 180c), to which the top film (310) has been peeled off, such that the opening (135) in the lid of the housing is the same opening via which the milk sample is supplied, and ii) enable an image of the one dry stick to be taken by the camera through the opening (135) for processing to determine the biomarker in the milk sample,
wherein the rear part (410) comprises:
an aperture (460) extending through the rear part (410), the rear part (410) being configured to receive a liquid evacuator (195) through the aperture (460);
a rear tape distributing spool holding member (510a), arranged to hold the tape distributing spool (131);
a rear tape collecting holding member (520a), arranged to hold the tape collecting spool (132);
a rear capstan reel holding member (530a), arranged to hold the capstan reel (370); and
a rear top film reel holding member (540a), arranged to hold the top film reel (330); and
wherein the frontal part (420) comprises:
a frontal tape distributing spool holding member (520b), arranged to hold the tape distributing spool (131) such that the rear tape distributing spool holding member (510a) and the frontal tape distributing spool holding member (520b) together hold the tape distributing spool (131);
a frontal tape collecting holding member (510b), arranged to hold the tape collecting spool (132) such that rear tape collecting holding member (520a) and the frontal tape collecting holding member (510b) together hold the tape collecting spool (132);
a frontal capstan reel holding member (540b), arranged to hold the capstan reel (370) such that the rear tape collecting holding member (520a) and the frontal capstan reel holding member (540b) together hold the capstan reel (370); and
a frontal top film reel holding member (530b), arranged to hold the top film reel (330) such that the rear top film reel holding member (540a) and the frontal top film reel holding member (530b) together hold the top film reel (330).

2. The cassette (130) according to claim 1, wherein the top lid (380) comprises a pressure exertion member (382) arranged to act on the tape (170) to keep the tape at a predetermined distance from the top lid (380) and keep that tape (170), and thereby the one of the dry sticks (180a, 180b, 180c), at a constant distance from the opening (135).

3. The cassette (130) according to claim 1, wherein the top lid (380) is configured to act on the tape (170) to keep the advancement apertures (175) on the tape (170) in place at the teeth (375) on the capstan reel (370).

4. The cassette (130) according to claim 1, further comprising:
at least one driving belt (450) located within the housing, the at least one driving belt (450) arranged to convey driving motion from the capstan reel (370), to at least one of the spools (131, 132).

5. The cassette (130) according to claim 4, wherein the driving belt (450) is arranged to convey the driving motion from the capstan reel (370) to the tape collecting spool (132).

6. The cassette (130) according to claim 1, wherein the rear part (410) comprises at least one ventilation aperture (390).

7. The cassette (130) according to claim 1, wherein the tape collecting spool (132) comprises guiding edges (440) arranged to fixate the tape (170) on the tape collecting spool (132) during collection of the tape (170).

8. A cassette (130) configured to enable measurement of at least one biomarker value of a milk sample of milk extracted by a milking equipment (110) from an animal (100), the milking equipment (110) providing extracted milk to a service module (120) having a camera (210); the cassette (130) comprising:
a housing providing the cassette with an interior volume, the housing being insertable into the service module (120), the housing comprising a top lid (380) having an opening (135),
wherein, the opening (135) of the housing is a camera alignment opening;
a tape distributing spool (131) located within the housing;
a tape (170) rolled up on the tape distributing spool (131), the tape (170) comprising a plurality of dry sticks (180a, 180b, 180c), configured to indicate the biomarker value of the milk sample, and a top film (310) arranged to protect the dry sticks (180a, 180b, 180c) while rolled up on the tape distributing spool (131), the tape (170) being advanceable within the housing so that each of the dry sticks (180a, 180b, 180c) are individually aligned with the opening (135) to respectively receive the milk sample when in alignment with the opening (135) onto each of the dry sticks (180a, 180b, 180c) and so that each of the dry sticks (180a, 180b, 180c) are subsequently individually aligned with the opening (135);

a tape collecting spool (132) located within the housing, the tape collecting spool (132) configured to collect the tape (170) with used dry sticks (180a, 180b, 180c);

a top film reel (330) located within the housing, the top film reel arranged to peel off and collect the top film (310) of the tape (170); and a capstan reel (370) comprising teeth (375), for engaging with advancement apertures (175) on the tape (170), wherein the tape (170) extends in a trajectory between the tape distributing spool (131) and the capstan reel (370), wherein the opening (135) is located above the tape (170) and vertically aligned with one of the dry sticks (180a, 180b, 180c) with the one of the dry sticks (180a, 180b, 180c) being visible through the opening (135), wherein the tape (170) is located above the tape distributing spool (131) and the tape collecting spool (132) such that the tape (170) is positioned with respect to the opening (135) to i) enable a needle (350) of a dosing module (137) to be inserted through the opening (135) for applying the milk sample of the animal (100) to the one of the dry sticks (180a, 180b, 180c), to which the top film (310) has been peeled off, such that the opening in the lid of the housing is the same opening via which the milk sample is supplied, and ii) to enable an image of the one dry stick to be taken by the camera through the opening (135) for processing to determine the biomarker in the milk sample, wherein the housing comprises a rear part (410) and a frontal part (420), the rear part (410) comprising:
  an aperture (460) extending through the rear part (410), the rear part (410) being configured to receive a liquid evacuator (195) through the aperture (460);
  a rear tape distributing spool holding member (510a), arranged to hold the tape distributing spool (131);
  a rear tape collecting holding member (520a), arranged to hold the tape collecting spool (132);
  a rear capstan reel holding member (530a), arranged to hold the capstan reel (370); and
  a rear top film reel holding member (540a), arranged to hold the top film reel (330); and the frontal part (420) comprising:
  a frontal tape distributing spool holding member (520b), arranged to hold the tape distributing spool (131);
  a frontal tape collecting holding member (510b), arranged to hold the tape collecting spool (132);
  a frontal capstan reel holding member (540b), arranged to hold the capstan reel (370); and
  a frontal top film reel holding member (530b), arranged to hold the top film reel (330), wherein the top lid (380) forms a side of the housing extending between the rear part (410) and the frontal part (420), wherein the top lid (380) comprises a pressure exertion member (382) arranged to act on the tape (170) to keep the tape at a predetermined distance from the top lid (380) and keep that tape (170), and thereby the one of the dry sticks (180a, 180b, 180c), at a constant distance from the opening (135).

9. The cassette (130) according to claim 1,
wherein the capstan reel (370) moves and advances the tape (170) from the tape distributing spool (131) to the collecting spool (132) when the capstan reel (370) is rotated, and
wherein at least a portion of the top film reel (330) is located vertically above the capstan reel (370) and above an upper surface of the tape (170) extending in the trajectory between the tape distributing spool (131) and the capstan reel (370).

10. The cassette (130) according to claim 9, further comprising:
  at least one driving belt (450) located within the housing, the at least one driving belt (450) arranged to convey driving motion from the capstan reel (370) to at least one of the tape distributing spool (131) and the collecting spool (132) when the capstan reel (370) is rotated,
  wherein the rear part (410) further comprises a first drive axle interface (470) arranged to rotate the capstan reel (370), and
  wherein the at least one driving belt (450) is arranged to convey the driving motion from the capstan reel (370) to the tape collecting spool (132).

11. The cassette (130) according to claim 10, wherein the rear part (410) first comprises a second drive axle interface (480) arranged to rotate the top film reel (330).

12. The cassette (130) according to claim 1, wherein the top film (310) is arranged to protect the dry sticks (180a, 180b, 180c), while rolled up on the tape distributing spool (131), from affection of humidity.

13. A cassette (130) configured to enable measurement of at least one biomarker value of a milk sample of milk extracted by a milking equipment (110) from an animal (100), the milking equipment (110) providing extracted milk to a service module (120) having a camera (210);
  the cassette (130) being disposable and comprising:
  a housing providing the cassette with an interior volume, the housing being insertable into the service module (12),
  wherein the housing comprises a top lid (380) having an opening (135), a rear part (410), and a frontal part (420),
  the top lid (380) forming a side of the housing extending between the rear part (410) and the frontal part (420),
  the rear part (410), the frontal part (420), the top lid (380) each being made of plastic;
  wherein, the opening (135) of the housing is a camera alignment opening;
  a tape distributing spool (131) located within the housing;
  a tape (170) rolled up on the tape distributing spool (131), the tape (170) comprising a plurality of dry sticks (180a, 180b, 180c), configured to indicate the biomarker value of the milk sample, and a top film (310) arranged to protect the dry sticks (180a, 180b, 180c) while rolled up on the tape distributing spool (131), the tape (170) comprising advancement apertures (175) and being advanceable within the housing so that each of the dry sticks (180a, 180b, 180c) are individually aligned with the opening (135) to respectively receive the milk sample when in alignment with the opening (135) onto each of the dry sticks (180a, 180b, 180c) and so that each of the dry sticks (180*a*, 180*b*, 180*c*) are subsequently individually aligned with the opening (135);
a tape collecting spool (132) located within the housing, the tape collecting spool (132) configured to collect the tape (170) with used dry sticks (180*a*, 180*b*, 180*c*);
a top film reel (330) located within the housing, the top film reel arranged to peel off and collect the top film (310) of the tape (170); and
a capstan reel (370) comprising teeth (375), for engaging with the advancement apertures (175) on the tape (170),
wherein the tape (170) extends in a trajectory between the tape distributing spool (131) and the capstan reel (370),
wherein the opening (135) is located above the tape (170) and vertically aligned with one of the dry sticks (180*a*, 180*b*, 180*c*) with the one of the dry sticks (180*a*, 180*b*, 180*c*) being visible through the opening (135),
wherein the tape (170) is located above the tape distributing spool (131) and the tape collecting spool (132) such that the tape (170) is positioned with respect to the opening (135) to i) enable a needle (350) of a dosing module (137) to be inserted through the opening (135) for applying the milk sample of the animal (100) to the one of the dry sticks (180*a*, 180*b*, 180*c*), to which the top film (310) has been peeled off, such that the opening (135) in the lid of the housing is the same opening via which the milk sample is supplied, and ii) enable an image of the one dry stick to be taken by the camera through the opening (135) for processing to determine the biomarker in the milk sample,
wherein the rear part (410) comprises:
an aperture (460) extending through the rear part (410), the rear part (410) being configured to receive a liquid evacuator (195) through the aperture (460);
a rear tape distributing spool holding member (510*a*), arranged to hold the tape distributing spool (131);
a rear tape collecting holding member (520*a*), arranged to hold the tape collecting spool (132);
a rear capstan reel holding member (530*a*), arranged to hold the capstan reel (370); and
a rear top film reel holding member (540*a*), arranged to hold the top film reel (330); and wherein the frontal part (420) comprises:
a frontal tape distributing spool holding member (520*b*), arranged to hold the tape distributing spool (131) such that the rear tape distributing spool holding member (510*a*) and the frontal tape distributing spool holding member (520*b*) together hold the tape distributing spool (131);
a frontal tape collecting holding member (510*b*), arranged to hold the tape collecting spool (132) such that rear tape collecting holding member (520*a*) and the frontal tape collecting holding member (510*b*) together hold the tape collecting spool (132);
a frontal capstan reel holding member (540*b*), arranged to hold the capstan reel (370) such that the rear tape collecting holding member (520*a*) and the frontal capstan reel holding member (540*b*) together hold the capstan reel (370);
a frontal top film reel holding member (530*b*), arranged to hold the top film reel (330) such that the rear top film reel holding member (540*a*) and the frontal top film reel holding member (530*b*) together hold the top film reel (330); and
at least one driving belt (450) located within the housing, the at least one driving belt (450) arranged to convey driving motion from the capstan reel (370) to at least one of the tape distributing spool (131) and the collecting spool (132) when the capstan reel (370) is rotated,
wherein the rear part (410) further comprises a first drive axle interface (470) arranged to rotate the capstan reel (370), and
wherein the at least one driving belt (450) is arranged to convey the driving motion from the capstan reel (370) to the tape collecting spool (132) such that the capstan reel (370) moves and advances the tape (170) from the tape distributing spool (131) to the collecting spool (132) when the capstan reel (370) is rotated.

14. The cassette (130) according to claim 13, wherein the rear part (410) first comprises a second drive axle interface (480) arranged to rotate the top film reel (330).

* * * * *